United States Patent [19]

Nelson et al.

[11] 4,041,173
[45] Aug. 9, 1977

[54] 2-CARBOXY-(7-,8- AND 9-SUBSTITUTED)-5-OXO-5H-DIBENZO (a,d) CYCLOHEPTENES AND THE CORRESPONDING 10,11-DIHYDRO COMPOUNDS

[75] Inventors: Peter H. Nelson; Karl G. Untch, both of Los Altos, Calif.

[73] Assignee: Syntex (U.S.A.) Inc., Palo Alto, Calif.

[21] Appl. No.: 619,723

[22] Filed: Oct. 6, 1975

[51] Int. Cl.[2] .............................................. C07C 63/44
[52] U.S. Cl. ................................... 424/308; 424/250;
424/253; 424/267; 424/287; 424/289; 424/295;
424/296; 424/317; 260/253; 260/268 TR;
260/293.62; 260/343.6; 260/269; 260/429 CY;
260/429.9; 260/438.1; 260/439 CY; 260/448 R;
260/501.1; 260/515 R; 542/449; 544/154
[58] Field of Search ............... 260/469, 247.2, 439,
260/429.9, 438.1, 448, 429, 515, 501.5, 309.6,
326.33, 268, 501.13; 424/293.62, 308, 317

[56] References Cited
U.S. PATENT DOCUMENTS

| 3,780,061 | 12/1973 | Allais et al. ........................... 260/469 |
| 3,803,234 | 4/1974 | Dostert et al. ......................... 260/469 |
| 3,933,905 | 1/1976 | Brunet et al. .......................... 260/469 |

*Primary Examiner*—John D. Randolph
*Attorney, Agent, or Firm*—Tom M. Moran

[57] ABSTRACT

A compound selected from the group of compounds represented by the formula

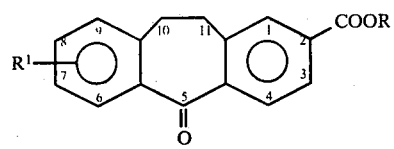

R is hydrogen, alkyl having 1 to 12 carbon atoms, or

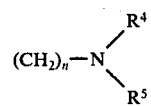

where n is an integer of 2 to 4 inclusive and $R^4$ and $R^5$ are independently lower alkyl of 1 to 6 carbon atoms inclusive or together $R^4$ and $R^5$ and the nitrogen atom to which they are attached form a heterocyclic ring having 5 to 6 total ring atoms;
$R^1$ is at the 7, 8 or 9 position and is halogen, hydroxy, lower alkoxy of 1 to 6 carbon atoms inclusive, or lower alkyl of 1 to 4 carbons atoms, inclusive;
the dotted lines may be an additional, optional bond between the carbon atoms at the 10- and 11- positions; and
the pharmaceutically acceptable salts thereof. The compounds are used pharmaceutically to treat allergic reactions and autoimmune diseases.

13 Claims, No Drawings

2-CARBOXY-(7-,8- AND 9-SUBSTITUTED)-5-OXO-5H-DIBENZO (a,d) CYCLOHEPTENES AND THE CORRESPONDING 10,11-DIHYDRO COMPOUNDS

BACKGROUND OF THE INVENTION

1. Field of the Invention

This invention relates to novel chemical compounds and the preparation thereof, their use as therapeutic agents, and their formulation as pharmaceutical compositions. More particularly, this invention relates to novel 2-carboxy-5-oxo-5H-dibenzo [a,d]cycloheptenes and the corresponding 10,11-dihydro compounds which are substituted at the 7,8 or 9 position with a halogen, hydroxy, lower alkyl, or lower alkoxy, and the pharmaceutically acceptable esters and salts thereof. The compounds are useful for the treatment of auto-immune diseases and allergic reactions when administered with suitable pharmaceutical excipients.

2. Prior Art

It is known that 5H-dibenzo[a,d]cycloheptenones are useful as precursors in the preparation of pharmacologically active compounds, and, in particular, they are useful in the preparation of compounds having tranquilizing, anti-depressant, analgesic, anti-inflammatory, psychotropic, anti-convulsants and anti-histaminic activity. See for example U.S. Pat. No. 3,551,498 to Tristrom et al of Merck; U.S. Pat. No. 3,256,335 to Slates et al of Merck; British 994,485 to Pfizer; U.S. Pat. No. 3,780,061 to Allais; British 1,076,612 to Merck; U.S. Pat. No. 3,803,234 to Dostert et al of Hoffman La Roche and Journal of Organic Chemistry, 27, 230–240, (1962), "New Psychotropic Agents Derivatives of Dibenzo [a,d]-1,4-cycloheptadiene" by Winthrop et al of Ayerst Research Labs.

In U.S. Pat. No. 3,780,061 the compound 5-oxo-8-chloro-10,11-dihydro-5H-dibenzo[a,d]cycloheptene-3-carboxylic acid is disclosed as an intermediate for the preparation of the corresponding 3-acetic acid, an analgesic or anti-inflammatory. No therapeutic utility is given for this intermediate or for other intermediates in the other patents cited.

Surprisingly, we have now discovered that the specific 2-carboxy-5-oxo-5H-dibenzo[a,d]cycloheptene and the corresponding 10,11-dihydro compounds which are substituted at the 7, 8 or 9 position with halogen, hydroxy, lower alkyl, or lower alkoxy show therapeutic activity in the treatment of auto-immune diseases and allergic reactions. The compounds of this invention are undisclosed in the prior and the most closely related compound disclosed in U.S. Pat. No. 3,780,061 is not shown to have therapeutic activity.

SUMMARY OF THE INVENTION

The novel 7, 8 or 9 substituted 2-carboxy-5-oxo-5H-dibenzo[a,d]cycloheptenes and 2-carboxy-10,11-dihydro-5-oxo-5H-dibenzo[a,d]cycloheptenes of the present invention are represented by the following formula:

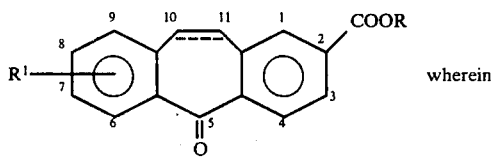

wherein

R is hydrogen, alkyl having 1 to 12 carbon atoms, or

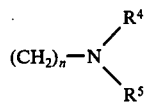

where $n$ is an integer of 2 to 4 inclusive and $R^4$ and $R^5$ are independently lower alkyl having 1 to 6 carbon atoms or together $R^4$ and $R^5$ and the nitrogen atom to which they are attached form a heterocyclic ring having 5 or 6 total ring atoms;

$R^1$ is at the 7, 8 or 9 position and is halogen, hydroxy, lower alkoxy of 1 through 6 carbons, or lower alkyl of 1 through 4 carbons, the dotted line refers to an additional, optional bond between the carbon atoms at the 10- and 11- positions; and the pharmaceutically acceptable salts thereof when R is hydrogen.

Another aspect of this invention is the use of the compounds set forth above in the treatment or prevention of auto-immune diseases and allergic reactions.

Still another aspect of the invention is the pharmaceutical composition which comprises a compound in combination with a suitable pharmaceutical excipient.

PREFERRED EMBODIMENTS

The Compounds

As used in this specification and claims, the term "alkyl" refers to both straight and branched alkyl groups having the number of carbon atoms indicated, and thus includes primary, secondary and tertiary alkyl groups. Typical alkyls of 1 to 12 carbons include for example, methyl, ethyl, n-propyl, isopropyl, n-butyl, isobutyl, t-butyl, n-amyl, n-hexyl, octyl, decyl, dodecyl, and the like.

The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, copper, zinc, manganous, aluminum, ferric, manganic salts and the like. Of these, sodium, potassium, ammonium, calcium, and magnesium are preferred. Salts derived from pharmaceutically acceptable organic non-toxic bases include salts of primary, secondary, tertiary and quaternary amines, substituted amines including naturally occurring substituted amines, cyclic amines and basic ion exchange resins, such as diethylamine, triethylamine, tripropylamine, 2-dimethylaminoethanol, 2-diethylaminoethanol, ethanolamine, tromethamine, lysine, arginine, histidine, caffeine, procaine, N-ethylpiperidine, hydrabamine, choline, betaine, ethylenediamine, glucosamine, methylglucamine, theobromine, purines, piperazine, piperidine, polyamine resins and the like. Particularly effective are the salts of ethanolamine, diethylamine, tromethamine, choline, and caffeine.

A particularly valuable group of compounds is represented by the formula

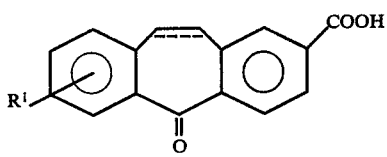

wherein R¹ is halogen. Another particulary suitable group of compounds and therefore preferred are those where there is only a single bond between the carbons at the 10- and 11-positions and R¹ is at the 7 or 9 position, especially where R¹ is a halogen such as fluoro, chloro, or bromo.

Thus, exemplary of the 2-carboxy compounds of the present invention, as represented by the structural formula above under "Summary of the Invention," are the illustrative compounds named below. For simplification, in naming the compounds falling within the scope of this invention, each of the names employed is meant to include and disclose 2 compounds. For example, the name "2-carboxy-7-fluoro(-10,11-dihydro)-5-oxo-5H-dibenzo[a,d]cycloheptene" discloses and names the following:

2-carboxy-7-fluoro-5-oxo-5H-dibenzo[a,d]cycloheptene; and
2-carboxy-7-fluoro-5-oxo-10,11-dihydro-5H-dibenzo[a,d]cycloheptene. A similar nomenclature is employed for the salts and esters.

Halogen substituted compounds 2-carboxy-8-fluoro-(10,11-dihydro)-5-oxo-5H-dibenzo[a,d]cycloheptene;
2-carboxy-8-chloro-(10,11-dihydro)-5-oxo-5H-dibenzo[a,d]cycloheptene;
2-carboxy-8-bromo-(10,11-dihydro)-5-oxo-5H-dibenzo[a,d]cycloheptene;
2-carboxy-8-iodo-(10,11-dihydro)-5-oxo-5H-dibenzo[a,d]cycloheptene; especially
2-carboxy-7-fluoro-(10,11-dihydro)-5-oxo-5H-dibenzo[a,d]cycloheptene;
2-carboxy-7-chloro-(10,11-dihydro)-5-oxo-5H-dibenzo[a,d]cycloheptene;
2-carboxy-7-bromo-(10,11-dihydro)-5-oxo-5H-dibenzo[a,d]cycloheptene;
2-carboxy-7-iodo-(10,11-dihydro)-5-oxo-5H-dibenzo[a,d]cycloheptene;
2-carboxy-9-fluoro-(10,11-dihydro)-5-oxo-5H-dibenzo[a,d]cycloheptene;
2-carboxy-9-chloro-(10,11-dihydro)-5-oxo-5H-dibenzo[a,d]cycloheptene;
2-carboxy-9-bromo-(10,11-dihydro)-5-oxo-5H-dibenzo[a,d]cycloheptene;
2-carboxy-9-iodo-(10,11-dihydro)-5-oxo-5H-dibenzo[a,d]cycloheptene;

Hydroxy substituted compounds 2-carboxy-7-hydroxy-(10,11-dihydro)-5-oxo-5H-dibenzo[a,d]cycloheptene;
2-carboxy-8-hydroxy-(10,11-dihydro)-5-oxo-5H-dibenzo[a,d]cycloheptene;
2-carboxy-9-hydroxy-(10,11-dihydro)-5-oxo-5H-dibenzo[a,d]cycloheptene;

Alkoxy substituted compounds 2-carboxy-8-methoxy-(10,11-dihydro)-5-oxo-5H-dibenzo[a,d]cycloheptene;
2-carboxy-8-n-butoxy-(10,11-dihydro)-5-oxo-5H-dibenzo[a,d]cycloheptene;
2-carboxy-8-n-hexoxy-(10,11-dihydro)-5-oxo-5H-dibenzo[a,d]cycloheptene; and especially
2-carboxy-7-methoxy-(10,11-dihydro)-5-oxo-5H-dibenzo[a,d]cycloheptene;
2-carboxy-7-ethoxy-(10,11-dihydro)-5-oxo-5H-dibenzo[a,d]cycloheptene;
2-carboxy-7-isopropoxy-(10,11-dihydro)-5-oxo-5H-dibenzo[a,d]-cycloheptene;
2-carboxy-7-n-butoxy-(10,11-dihydro)-5-oxo-5H-dibenzo[a,d]cycloheptene;
2-carboxy-7-isopentoxy-(10,11-dihydro)-5-oxo-5H-dibenzo[a,d]cycloheptene;
2-carboxy-7-n-hexoxy-(10,11-dihydro)-5-oxo-5H-dibenzo[a,d]cycloheptene;
2-carboxy-9-ethoxy-(10,11-dihydro)-5-oxo-5H-dibenzo[a,d]cycloheptene;
2-carboxy-9-isopropoxy-(10,11-dihydro)-5-oxo-5H-dibenzo[a,d]cycloheptene; and
2-carboxy-9-isopentoxy-(10,11-dihydro)-5-oxo-5H-dibenzo[a,d]cycloheptene.

Alkyl substituted compounds 2-carboxy-7-methyl-(10,11-dihydro)-5-oxo-5H-dibenzo[a,d]cycloheptene;
2-carboxy-7-ethyl-(10,11-dihydro)-5-oxo-5H-dibenzo[a,d]cycloheptene;
2-carboxy-7-propyl-(10,11-dihydro)-5-oxo-5H-dibenzo[a,d]cycloheptene;
2-carboxy-7-isopropyl-(10,11-dihydro)-5-oxo-5H-dibenzo[a,d]cycloheptene;
2-carboxy-8-methyl-(10,11-dihydro)-5-oxo-5H-dibenzo[a,d]cycloheptene;
2-carboxy-8-ethyl-(10,11-dihydro)-5-oxo-5-dibenzo[a,d]cycloheptene;
2-carboxy-8-isopropyl-(10,11-dihydro)-5-oxo-5H-dibenzo[a,d]cycloheptene;
2-carboxy-8-propyl-(10,11-dihydro)-5-oxo-5H-dibenzo[a,d]cycloheptene;
2-carboxy-9-methyl-(10,11-dihydro)-5-oxo-5H-dibenzo[a,d]cycloheptene;
2-carboxy-9-ethyl-(10,11-dihydro)-5-oxo-5H-dibenzo[a,d]cycloheptene;
2-carboxy-9-propyl-(10,11-dihydro)-5-oxo-5H-dibenzo[a,d]cycloheptene; and
2-carboxy-9-isopropyl-(10,11-dihydro)-5-oxo-5H-dibenzo[a,d]cycloheptene.

Suitable Pharmaceutical Salts

The sodium salt of 2-carboxy-9-chloro-(10,11-dihydro)-5-oxo-5H-dibenzo[a,d]cycloheptene;
the potassium salt of 2-carboxy-9-bromo-(10,11-dihydro)-5-oxo-5H-dibenzo[a,d]cycloheptene;
the potassium salt of 2-carboxy-7-chloro-(10,11-dihydro)-5-oxo-5H-dibenzo[a,d]cycloheptene;
the ammonium salt of 2-carboxy-8-bromo-(10,11-dihydro)-5-oxo-5H-dibenzo[a,d]cycloheptene;
the ammonium salt of 2-carboxy-9-iodo-(10,11-dihydro)-5-oxo-5H-dibenzo[a,d]cycloheptene;
the calcium salt of 2-carboxy-7-bromo-(10,11-dihydro)-5-oxo-5H-dibenzo[a,d]cycloheptene;
the magnesium salt of 2-carboxy-7-iodo-(10,11-dihydro)-5-oxo-5H-dibenzo[a,d]cycloheptene;
the ethanolamine salt of 2-carboxy-7-fluoro-(10,11-dihydro)-5-oxo-5H-dibenzo[a,d]cycloheptene;
the diethylamine salt of 2-carboxy-7-chloro-(10,11-dihydro)-5-oxo-5H-dibenzo[a,d]cycloheptene;

the tromethamine salt of 2-carboxy-9-bromo-(10,11-dihydro)-5-oxo-5H-dibenzo[a,d]cycloheptene;

the choline salt of 2-carboxy-7-iodo-(10,11-dihydro)-5-oxo-5H-dibenzo[a,d]cycloheptene;

the caffeine salt of 2-carboxy-9-fluoro-(10,11-dihydro)-5-oxo-5H-dibenzo[a,d]cycloheptene;

the procaine salt of 2-carboxy-8-bromo-(10,11-dihydro)-5-oxo-5H-dibenzo[a,d]cycloheptene;

the sodium salt of 2-carboxy-7-hydroxy-(10,11-dihydro)-5-oxo-5H-dibenzo[a,d]cycloheptene;

the potassium salt of 2-carboxy-7-methoxy-(10,11-dihydro)-5-oxo-5H-dibenzo[a,d]cycloheptene;

the ammonium salt of 2-carboxy-9-isopropoxy-(10,11-dihydro)-5-oxo-5H-dibenzo[a,d]cycloheptene;

the calcium salt of 2-carboxy-7-ethoxy-(10,11-dihydro)-5-oxo-5H-dibenzo[a,d]cycloheptene;

the magnesium salt of 2-carboxy-9-methyl-(10,11-dihydro)-5-oxo-5H-dibenzo[a,d]cycloheptene;

the ammonium salt of 2-carboxy-7-isopropyl-(10,11-dihydro)-5-oxo-5H-dibenzo[a,d]cycloheptene;

the ethanolamine salt of 2-carboxy-7-hydroxy-(10,11-dihydro)-5-oxo-5H-dibenzo[a,d]cycloheptene;

the tromethamine salt of 2-carboxy-9-hydroxy-(10,11-dihydro)-5-oxo-5H-dibenzo[a,d]cycloheptene;

the choline salt of 2-carboxy-7-methoxy-(10,11-dihydro)-5-oxo-5H-dibenzo[a,d]cycloheptene;

the procaine salt of 2-carboxy-9-isopropoxy-(10,11-dihydro)-5-oxo-5H-dibenzo[a,d]cycloheptene;

the ethanolamine salt of 2-carboxy-7-methyl-(10,11-dihydro)-5-oxo-5H-dibenzo[a,d]cycloheptene;

the tromethamine salt of 2-carboxy-9-n-propyl-(10,11-dihydro)-5-oxo-5H-dibenzo[a,d]cycloheptene;

the choline salt of 2-carboxy-7-isopropyl-(10,11-dihydro)-5-oxo-5H-dibenzo[a,d]cycloheptene;

Suitable Pharmaceutical Esters

The methyl ester of 2-carboxy-9-chloro-(10,11-dihydro)-5-oxo-5H-dibenzo[a,d]cycloheptene;

the ethyl ester of 2-carboxy-8-chloro-(10,11-dihydro)-5-oxo-5H-dibenzo[a,d]cycloheptene;

the n-propyl ester of 2-carboxy-9-bromo-(10,11-dihydro)-5-oxo-5H-dibenzo[a,d]cycloheptene;

the isopropyl ester of 2-carboxy-7-chloro-(10,11-dihydro)-5-oxo-5H-dibenzo[a,d]cycloheptene;

the n-butyl ester of 2-carboxy-8-bromo-(10,11-dihydro)-5-oxo-5H-dibenzo[a,d]cycloheptene;

the n-butyl ester of 2-carboxy-9-iodo-(10,11-dihydro)-5-oxo-5H-dibenzo[a,d]cycloheptene;

the n-amyl ester of 2-carboxy-7-bromo-(10,11-dihydro)-5-oxo-5H-dibenzo[a,d]cycloheptene;

the isoamyl ester of 2-carboxy-8-fluoro-(10,11-dihydro)-5-oxo-5H-dibenzo[a,d]cycloheptene;

the n-hexyl ester of 2-carboxy-7-fluoro-(10,11-dihydro)-5-oxo-5H-dibenzo[a,d]cycloheptene;

the n-heptyl ester of 2-carboxy-8-chloro-(10,11-dihydro)-5-oxo-5H-dibenzo[a,d]cycloheptene;

the n-decyl ester of 2-carboxy-9-bromo-(10,11-dihydro)-5-oxo-5H-dibenzo[a,d]-cycloheptene;

the dodecyl ester of 2-carboxy-7-iodo-(10,11-dihydro)-5-oxo-5H-dibenzo[a,d]cycloheptene;

the methyl ester of 2-carboxy-7-hydroxy-(10,11-dihydro)-5-oxo-5H-dibenzo[a,d]cycloheptene;

the ethyl ester of 2-carboxy-8-methoxy-(10,11-dihydro)-5-oxo-5H-dibenzo[a,d]cycloheptene;

the n-propyl ester of 2-carboxy-9-isopropoxy-(10,11-dihydro)-5-oxo-5H-dibenzo[a,d]cycloheptene;

the isopropyl ester of 2-carboxy-7-ethoxy-(10,11-dihydro)-5-oxo-5H-dibenzo[a,d]cycloheptene;

the t-butyl ester of 2-carboxy-9-methyl-(10,11-dihydro)-5-oxo-5H-dibenzo[a,d]cycloheptene;

the n-amyl ester of 2-carboxy-7-isopropyl-(10,11-dihydro)-5-oxo-5H-dibenzo[a,d]cycloheptene; and the isoamyl ester of 2-carboxy-8-ethyl-(10,11-dihydro)-5-oxo-5H-dibenzo[a,d]cycloheptene;

Process Of Preparation

The compounds of this invention may be prepared by several routes;

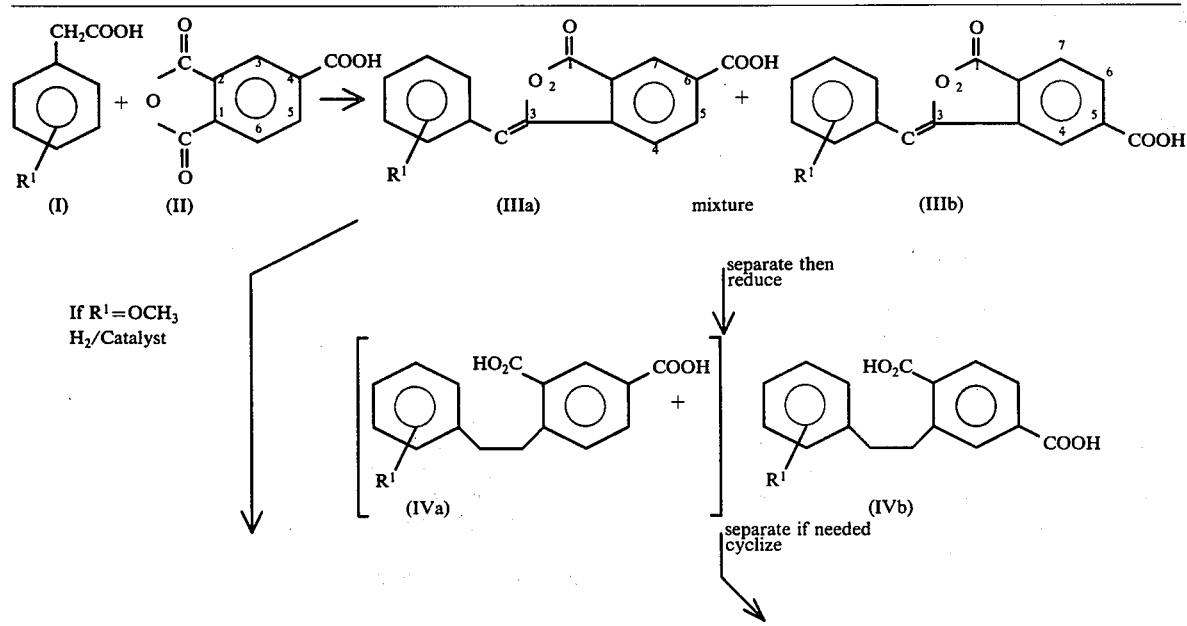

A. Phenylacetic Acid Route

A. Phenylacetic Acid Route

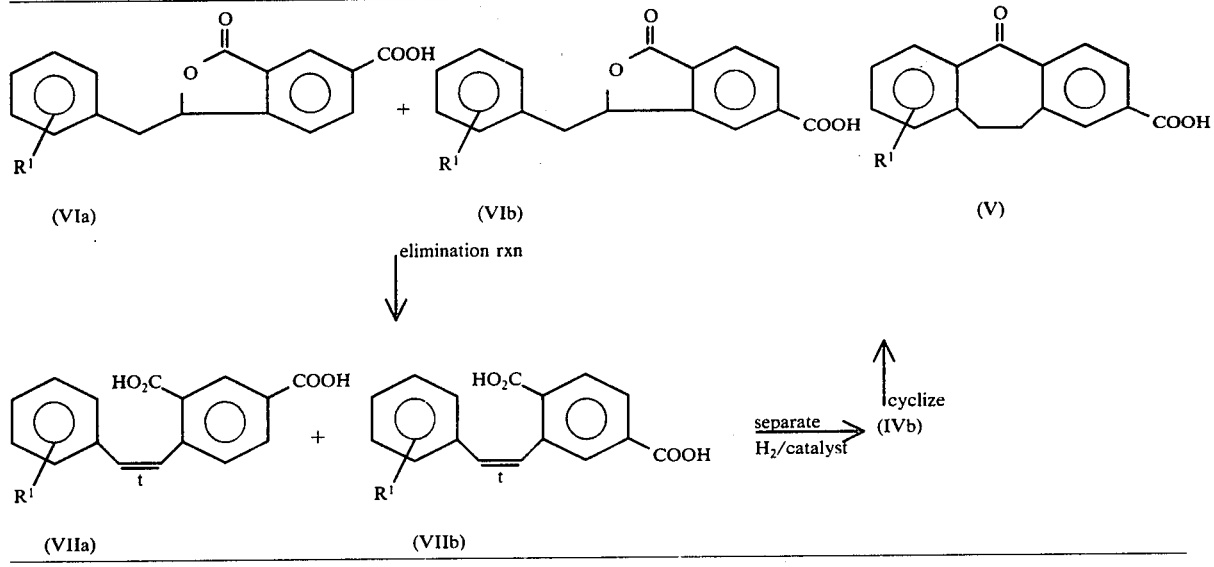

By this method (schematically shown above) a 2-, 3- or 4- substituted phenylacetic acid (I) is reacted with benzene 1,2,4-tri-carboxylic anhydride (II) in about equimolar amounts at a temperature of about 200° to 280° C in the presence of a suitable catalyst such as potassium acetate, sodium acetate or the sodium or potassium salt of the phenylacetic acid used. This results in a mixture of 3-(2-, 3- or 4-substituted benzylidene) phthalide-6-carboxylic acid (IIIa) and -5-carboxylic acid (IIIb).

The resulting mixture may be separated into the two position isomers immediately using fractional crystallization techniques or chromatographic techniques which are known in the art to obtain the phthalide-5-carboxylic acid (IIIb) which is then reduced to form a 2-(2-, 3- or 4-substituted phenethyl)benzene-1,4-dicarboxylic acid (IVb) using a suitable reducing agent along with an appropriate solvent at reflux conditions, that is about 100° to 170° C. Red phosphorus/aqueous hydriodic acid is particularly suitable for this reduction, while useful co-solvents include acetic acid, propionic acid and the corresponding anhydrides thereof.

The resulting 1,4-dicarboxylic acid (IVb) is then cyclized to the desired 2-carboxy-7-, 8- or 9-substituted -10,11-dihydro-5-oxo-5H-dibenzo[a,d]cycloheptene (V). The cyclization reaction can take place by contacting 1,4-dicarboxylic acid (IVb) with a suitable acid such as sulfuric acid or polyphosphoric alone or in a co-solvent such as tetrahydrothiophene-1,1-dioxide, or by using phosphorus pentoxide in nitrobenzene. Preferably polyphosphoric acid is employed because of the ease of utilizing the acid, and in such a case the reaction is carried out at temperatures ranging from about 50° to 190° C depending, i.a., on the substituents on the substituted phenylethyl group.

In some cases it may be desireable to cyclize the 1,4-dicarboxylic acid (IVb) by first converting it to the acid chloride, treating the acid chloride with a Lewis acid such as anhydrous aluminium chloride to give after base hydrolysis the desired product.

If the mixture of the 6-carboxyphthalide (IIIa) and 5-carboxyphthalide (IIIb) is not first separated as described above, the mixture may be reduced by the same process set forth previously to give a mixture of the 1,4-dicarboxylic acid (IVb) along with the 4-(2-, 3- or 4-substituted phenethyl)-1,3-dicarboxylic acid (IVa) which mixture is then separated by conventional means such as fractional crystallization to give the 1,4-dicarboxylic acid (IVb) alone which is then cyclized to give the desired product of this invention as discussed above.

If the starting material (I) is a methoxyphenylacetic acid, particularly 4-methoxyphenylacetic acid, after the mixture of the 5- and 6-carboxyphthalides (IIIb and IIIa respectively) is obtained from the condensation with benzene-1,2,4-tricarboxylic anhydride, the mixture is first catalytically hydrogenated using a suitable noble metal catalyst such as palladium on carbon or platinum oxide in the presence of molecular hydrogen at a temperature of about 25° and at atmospheric pressure. Alternatively the hydrogenation may be carried out by a chemical means using for example diimide. Hydrogenation results in a mixture of 3-(2-, 3-, or 4-methoxybenzyl)-5-carboxyphthalide (VIb) and 3-(2-, 3-, or 4-methoxybenzyl)-6-carboxyphthalide (VIa). The phthalide mixture then undergoes an elimination reaction to sever the lactone ring and obtain a mixture of trans-1-(methoxyphenyl)-2-(2,4-dicarboxyphenyl)ethylene (VIIa) and the corresponding trans-2-(2,5-dicarboxyphenyl)ethylene (VIIb). The elimination reaction may be carried out by any suitable means known in the art but potassium t-butoxide in dimethyl sulfoxide is found to be particularly suitable. Generally the reaction is carried out with 3 molar quantities of potassium t-butoxide and an excess of dimethylsulfoxide. The two position isomers VIIa and VIIb are then separated by suitable fractional crystallization methods to obtain the desired isomer (VIIb) alone and this isomer is then hydrogenated using a suitable noble metal catalyst such as palladium on carbon or platinum oxide in the presence of molecular hydrogen to give 2-(methoxyphenethyl)-terephthalic acid (IVb) which in turn is cyclized as discussed above to give the 2-carboxy 7,8 or 9-methoxy-10,11-dihydro-5-oxo-5H-dibenzo[a,d]cycloheptene (V).

B. Base—catalyzed condensation

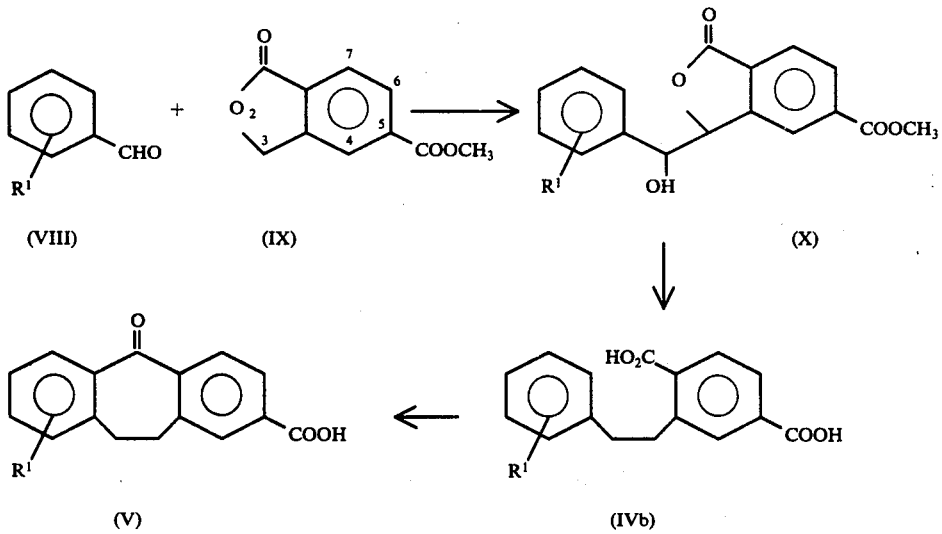

In this method a 2-, 3- or 4-substituted benzaldehyde (VIII) is condensed with 5-carbomethoxyphthalide (IX) by reacting the two compounds in the presence of a suitable strong base in an appropriate solvent at temperatures from 0° to 100° C depending on the base and the substituent on the benzaldehyde. Suitable strong base and solvent combinations include sodium hydride in combination with an inert solvent such as tetrahydrofuran or dimethylformamide, sodium methoxide in methanol, or potassium t-butoxide in t-butanol or dimethylformamide. By this method either a carboxy or a carboalkoxy such as carbomethoxy can be on the 5 position of the phthalide ring. The base catalyzed condensation results in a 3-(2-, 3- or 4-substituted-alpha-hydroxy benzyl)-6-carbomethoxyphthalide (X) which is then reduced using a suitable reducing agent such as red phosphorus and hydriodic acid, optionally in the presence of a suitable solvent such as acetic acid, propionic acid, or the anhydrides thereof at reflux conditions such as 100° to 170° C. Preferably the compound does not have a methoxy group substituted thereon since the methoxy group will be converted to the corresponding hydroxy group during the reaction.

The reduction results in a 2-(2-, 3- or 4-substituted phenethyl) 1,4-dicarboxylic acid (IVb) which is then cyclized to give the compound of this invention represented by formula V. The cyclization may utilize any of the procedures set forth hereinbefore.

C. Wittig condensation route.

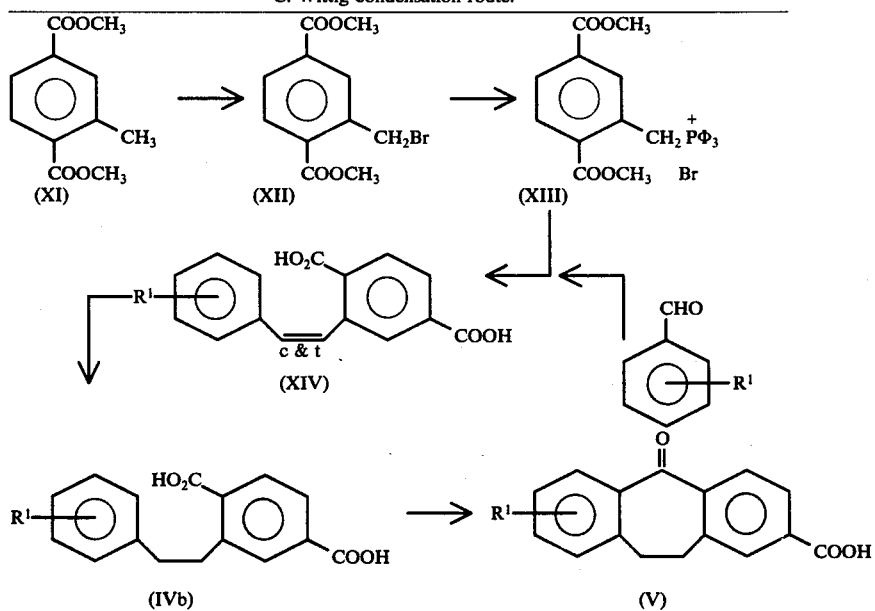

A particularly effective, and therefore preferred, method of preparing the compounds of this invention is by performing a Wittig condensation. By this process 2-methylterephthalic acid dimethylester (XI) is reacted with a suitable chlorinating or brominating agent such as N-bromosuccinimide or N-chlorosuccinimide to form 2-bromo(or chloro)methylterephthalic acid dimethyl ester (XII). This product is subsequently reacted with an effective organic phosphine such as tributylphosphine or, preferably, triphenylphosphine to afford 2,5-bis(carbomethoxy) benzyltriphenylphosphonium bromide or chloride (XIII) which is subsequently treated with a p-, m- or o- substituted benzaldehyde in a suitable base and inert solvent to afford, after alkaline hydrolysis, 2'-,3'- or 4'-substituted cis and trans stilbene-2,5-dicarboxylic acids (XIV). Suitable bases for this reaction may be sodium hydride, triethylamine, or preferably diazabicyclononene while a suitable inert solvent may inclue tetrahydrofuran, acetonitrile, or the like. The mixture of the cis and trans stilbenes (XIV) is then hydrogenated using molecular hydrogen under suitable hydrogenation conditions with a suitable noble metal catalyst such as palladium on carbon or platinum oxide until the theoretical amount of hydrogen has been absorbed by the compound. This hydrogenation affords a 2-(2-,3- or 4-substituted phenethyl)terephthalic acid (IVb). The resulting saturated compound is then cyclized by employing a suitable cyclizing agent as set forth in part A, above, to form V.

D. Preparation of 2-carboxy-7-,8- or 9-hydroxy or alkoxy-10,11-dihydro-5-oxo-5H-dibenzo[a,d]cycloheptene By using any of methods A, B or C to obtain a 2-carboxy-7-,8- or 9-methoxy-10,11-dihydro-5-oxo-5H-dibenzo[a,d]cycloheptene, the compound is treated for example with pyridine hydrochloride at a temperature of about 200° to 230° C, to prepare the corresponding 7-,8- or 9-hydroxy compound which is then reacted with a lower alkyl halide such as an alkyl chloride, alkyl iodide, alkyl bromide or dialkyl sulfate at reflux conditions in the presence of a strong base such as sodium hydroxide, potassium hydroxide, sodium carbonate or potassium carbonate in aqueous alcohol at reflux conditions to give the corresponding 7-8- or 9-alkoxy substituted compound.

E. Interconversion of 7-8- or 9-halo compounds

Once a 2-carboxy-7-,8- or 9-halo-10,11-dihydro-5-oxo-5H-dibenzo[a,d]cycloheptene is prepared by any of the methods A, B or C above, it may be converted to another 7-8- or 9-halo substituted compound by contacting the compound with an appropriate cuprous halide in the presence of a suitable solvent such as N-methylpyrrolidinone. For example a 7-chloro compound may be obtained from a 7-bromo compound by treating the 7-bromo compound with cuprous chloride in a suitable polar, high boiling solvent at 150° to 200° C. Such a solvent may be N-methylpyrrolidinone or dimethylformamide. Alternatively a 7-iodo compound may be prepared from a 7-bromo compound by treating the 7-bromo compound with cuprous iodide in the presence of N-methylpyrrolidinone.

F. Preparation of 2-carboxy-7-8- or 9-substituted-5-oxo-5H-dibenzo[a,d]cycloheptene Once a 10,11-dihydro compound is prepared by the methods set forth in parts A, B, C or E above, the unsaturated compound may be prepared by first esterifying the 2-carboxy group by any method known in the art. The esterification is carried out in order to increase the solubility of the compound in the reaction solvent as well as to eliminate side reactions from taking place at the carboxy group.

Once the 2-carboxy is esterified the compound is treated with a brominating or chlorinating agent such as N-bromosuccinimide or N-chlorosuccinimide to form an intermediate 10- or 11-chloro or bromo substituted compound. Once the 10- or 11-halogen compound is obtained it is treated to eliminate a hydrohalic acid and subsequently hydrolyzed to the 2-acid. This may be done in 1 or 2 steps.

In the 2 step process the 10- or 11-halogen substituted compound is treated with a suitable base such as diazabicyclononene in an appropriate solvent such as dimethylformamide or acetonitrile at 0° to 80° for a time sufficient to remove substantially all of the hydrohalic acid from the molecule. Once the acid has been removed and a double bond formed between the 10- and 11-carbon atoms the next step involves hydrolyzing the resulting compound under basic conditions to form the 2-carboxy compound.

In the one step process, the removal of the hydrohalic acid and hydrolysis may take place in one step by using a strong base such as sodium or potassium hydroxide in an aqueous alcoholic solution under reflux. This results in the formation of a double bond at the 10- and 11-carbons as well as the hydroylsis of the ester to form the free acid at the 2-position.

An alternative process comprises refluxing the acid or ester in benzene and a mixture of phosphorus pentachloride and phosphorus oxychloride. The resulting reaction mixture is then quenched with an aqueous alcohol mixture such as aqueous methanol to ultimately form the unsaturated 2-carboxy compound. The 2-carboxy-7,8, or 9-hydroxy-5-oxo-5H-dibenzo[a,d]cycloheptenes are preferably obtained by subjecting the corresponding 7-8-, or 9-methoxy compounds, obtained as described above, to the demethylation reaction described in D above.

G. Preparation of pharmaceutically acceptable esters and salts

The pharmaceutically acceptable salts are prepared by conventional techniques from pharmaceutically acceptable nontoxic bases, including metal salts such as sodium, potassium, calcium, aluminum and the like, as well as from organic amines, such as diethylamine, triethylamine, 2-dimethylaminoethanol, 2-diethylaminoethanol, ethanolamine, lysine, arginine, choline, histidine, caffeine, procaine, N-ethylpiperidine, hydrabamine and the like. The salts may be converted back to the free acid if desired by any appropriate procedure or may be converted to other salts.

The free acids can be esterified according to known procedures, for example, by treatment of the free acid or one of its functional derivatives, such as the acid chloride or the acid anhydride with an appropriate alcohol, in the presence of an acid, dehydrating, or basic catalyst. Other methods of esterification known to those skilled in this art can also be utilized.

Also included within the novel compounds of this invention are the corresponding dialkylaminoalkyl esters thereof which can be prepared for example by converting the free acid to the corresponding acid halide, as by treatment with thionyl chloride, and reacting the acid halide so produced with a hydroxyalkylamine, such as 2-dimethylaminoethanol or 2-diethylaminoethanol, to afford the compounds of the Formula set forth in this specification under "Summary of the Invention" wherein $R'$ is

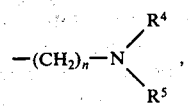

where $R^4$ and $R^5$ are independently lower alkyl. Or, the acid halide derivative can be reacted with a N-(ω-hydroxyalkyl)-heterocyclic amine to afford the compound of Formula I where $R^4$ and $R^5$ and the nitrogen atom to which they are attached for a heterocyclic ring. As used herein, the term "heterocyclic ring" refers to both unsubstituted and substituted heterocyclic rings containing at least one nitrogen ring atom and includes both saturated and unsaturated heterocyclic rings having 5 or 6 ring atoms. More specifically, the heterocyclic rings per se contemplated hereby have one nitrogen atom and four or five carbon atoms, two nitrogen atoms and three or four carbon atoms, or one nitrogen atom, one oxygen atom and four carbon atoms. Typical heterocyclic rings include, for example, 2-imidazolin-1-yl, 3-N-methyl-2-imidazolin-1-yl, pyrrolidinyl, 2-methyl-pyrrolidin-1-yl, morpholino, 3-methyl-morpholino, 4-N-methyl-piperazin-1-yl, 4-N-β-hydroxyethyl-piperazin-1-yl, piperidinyl, and the like. The esters may then be transesterified where appropriate or hydrolyzed back to the free acid.

In each of the process steps, described herein above and below, unless otherwise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the present invention but not specifically described in this specification, will be apparent to those skilled in this art.

Pharmaceutical Compositions

The pharmaceutical compositions of this invention include a conventional pharmaceutical excipient and an active compound of this invention, the excipient being solid or liquid. In addition, the pharmaceutical composition may include other medicinal agents, pharmaceutical agents, carriers, adjuvants, vehicles, etc.

For oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

An active compound of Formula I may be formulated into a suppository using, for example, polyalkylene glycols, for example, polypropylene glycol, as the carrier. Liquid pharmaceutically administerable compositions can, for example, be prepared by dissolving, dispersing, suspending, etc., an active compound of Formula I and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

In the treatment of asthmatic conditions, the compound of Formula I can be administered as above, and, in addition, by inhalation using either solid, liquid, aerosol, or suspensions as the dosage form.

Actual methods of preparing such dosage forms are known, or will be apparent, to those skilled in this art; for example, see Remington's *Pharmaceutical Sciences*, Mack Publishing Company, Easton, Pennsylvania, 14th. Edition, 1970. The composition to be administered will, in any event, contain a quantity of the active compound(s) in a pharmaceutically effective amount for relief of the particular condition being treated in accordance with the teachings of this invention.

Utility and Method of Treatment

The compounds of this invention are useful in the treatment of auto-immune diseases, for example, glomerulonephritis, lupus erythematosus and rheumatoid arthritis, and allergic reactions such as asthmatic attacks.

The 10,11-dihydro compounds of this invention are also useful as intermediates in the preparation of the corresponding 10,11-dihydro-5-oxo-5H-dibenzo[a,d]cycloheptene acetic or α-methyl or α-ethyl acetic acids as disclosed in Netherlands patent No. 7,402,475 to Rhone-Poulenc which show, i.a., anti-inflammatory activity.

The method of treatment comprises administering a biologically effective amount of a compound of this invention to an animal which requires it. Administration of the active compound of this invention in an appropriate pharmaceutical composition can be via any of the accepted modes of systemic administration of agents of this type. Thus, administration can be, for example, orally or parenterally, in the form of solid, semi-solid or liquid dosage forms, such as, for example, tablets, suppositories, pills, capsules, powders, liquid solutions, suspensions, or the like, preferably in unit dosage forms suitable for administration of precise dosages. In the treatment of asthmatic conditions, a compound of this invention may be administered by inhalation using either a solid, liquid, aerosol, or suspension.

The preferred manner of administration is oral using a convenient daily dosage regimen which can be adjusted according to the degree of affliction. Generally, a daily dose of from 0.1 mg. to 50 mg. of active compound of Formula I per kilogram of body weight is used, for example, in the range from 1 mg. to 10 mg. per kilogram of body weight per day.

The following examples are given to further elucidate specific reactants and reaction conditions which may be employed to obtain the compounds of this invention. The examples are representative only and are not meant to limit or restrict the scope of the subject matter set forth in the claims appended hereto.

EXAMPLE I — Phenylacetic acid route

A. Preparation of 2-carboxy-(7-and 8-halo)-10,11-dihydro-5oxo-5H-dibenzo[a,d]cycloheptenes A mixture of 103.2 g. of p-bromophenylacetic acid, 77.4 g. of benzene-1,2,4-tricarboxylic anhydride and 1.5 g. of sodium acetate was heated to 275° for 2 hours. The residue was dissolved in 1600 ml of hot dimethylformamide and the solution diluted with 400 ml of water, then cooled. The solution was then filtered to afford a mixture of 3-(p-bromobenzylidene)phthalide-5- and -6-carboxylic acids. 80 g. of this mixture was refluxed for 72 hours in 160 ml of acetic anhydride and 240 ml of 57% aqueous hydriodic acid containing 35.2 g. of red phosphorus. The mixture was cooled in ice and diluted with 1000 water. The solution was filtered and the residue dissolved in 800 ml dimethylformamide and filtered. The filtrate was evaporated to yield a residue which upon recrystallization from benzene: ethanol (3:1) yielded 4-(p-bromophenethyl)benzene-1,3-dicarboxylic acid. The mother liquors were evaporated and the residue recrystallized from ethyl acetate to afford 2-(p-bromophenethyl)benzene-1,4-dicarboxylic acid. 8.5 G. of 2-(p-bromophenethyl)-benzene-1,4-dicarboxylic acid was stirred at 170° for 6 hours in a mixture of 40 ml of polyphosphonic acid and 30 ml of tetrahydrothiophene-1,1-dioxide. The mixture was then poured into water and the product filtered off and recrystallized from aqueous dimethylformamide to yield 2-carboxy-7-bromo-10,11-dihydro-5-oxo-5H-dibenzo[a,d]cycloheptene mp 252°-254°.

Similarly, other 7-and 8-halo substituted compounds of this invention may be prepared according to the above procedure. For example, from m-bromophenylacetic acid, 2-carboxy-8-bromo-10,11-dihydro-5-oxo-5H-dibenzo[a,d]cycloheptene is obtained having a m.p. of 218°-219° C.

B. Preparation of 2-carboxy-7-,8- or 9-alkyl-10,11-dihydro-5-oxo-5H-dibenzo[a,d]cycloheptenes Benzene-1,2,4-tricarboxylic anhydride and p-isopropylphenylacetic acid are reacted together as described in Example IA to give a mixture of benzylidenephthalide carboxylic acids. Fractional crystallization of this mixture from aqueous ethanol yields 2-(p-ispropylbenzylidene)phthalide-5-carboxylic acid as the less soluble isomer, and 4-(p-isopropylbenzylidene)phthalide-6-carboxylic acid as the more soluble isomer. By following the rest of the procedure set forth in part A of this example, 2-carboxy-7-isopropyl-10,11-dihydro-5-oxo-5H-dibenzo[a,d]cycloheptene was obtained with a m.p. of 178°-182° C.

Similarly, other 7-,8- or 9 alkyl compounds of this invention may be prepared according to the above procedure. Exemplarly alkyl groups include methyl, ethyl, n-propyl, n-butyl, 2-butyl, n-pentyl, isopentyl, n-hexyl, and the like.

C. Preparation of 2-carboxy-7-methoxy-10,11-dihydro-5-oxo-5H-dibenzo[a,d]cycloheptene 45 G. of a mixture of 3-(p-methoxybenzylidene)phthalide-5- and -6- carboxylic acids, obtained by the condensation of p-methoxyphenylacetic acid and benzene-1,2,4-tricarboxylic anhydride as described in Example 1, was hydrogenated for 20 hours in 250 ml of dimethylformamide containing 10.5 g. of 10% palladium on carbon catalyst. The solution was filtered and the filtrate evaporated. The residue was recrystallized from aqueous acetic acid to afford 3-(p-methoxybenzyl)phthalide-5- and -6- carboxylic acids. 24.1 G of this mixture was dissolved in 90 ml of dimethylsulfoxide and 30 g. of potassium tertbutoxide was added. After 15 minutes the solution was poured into water, acidified with acetic acid, and the product filtered off. Fractional crystallization from dioxan afforded 4'-methoxy-trans-stilbene 2,4-dicarboxylic acid as the less soluble isomer, and 4'-methoxy-trans-stilbene-2,5-dicarboxylic acid as the more soluble isomer. 2.4 G. of 4'-methoxy-trans-stilbene-2,5-dicarboxylic acid was hydrogenated for 4-½ hours in 20 ml dimethylformamide and 20 ml of acetic acid containing 0.3 g. of 10% palladium on carbon catalyst. The solution was filtered and evaporated and the residue recrystallized from aqueous ethanol to afford 2-(4-methoxyphenethyl)benzene-1,4-dicarboxylic acid. This compound was then cyclized by the procedure of part A of this example to give 2-carboxy-7-methoxy-10,11-dihydro-5-oxo-5H-dibenzo[a,d]cycloheptene having a m.p of 201°-203° C.

EXAMPLE II — Base-catalyzed condensation 8.5 G. of 5-carbomethoxyphthalide and 2.43 g. of sodium methoxide were refluxed for 15 minutes in 250 ml of methanol, and then 5.55 g. of o-fluorobenzaldehyde was added. The mixture was refluxed for 20 hours and then poured into water and acidified with dilute hydrochloric acid. The solution was extracted with ethyl acetate and the extract washed, dried and evaporated. The residue was refluxed for 48 hours in 75 ml of acetic acid and 45 ml of 57% aqueous hydriodic acid containing 7.5 g. of red phosphorus. The mixture was poured into water and filtered. The residue was dissolved in ethanol and the solution filtered and evaporated to afford 2-(o-fluorophenethyl)benzene-1,4-dicarboxylic acid which was cyclized according to the method described in Example I, A to obtain 2-carboxy-9-fluoro-10,11-dihydro-5-oxo-5H-dibenzo[a,d]cycloheptene having a m.p. of 248.5° to 249.5° C.

Similarly, from o-bromobenzaldehyde, 2-carboxy-9-bromo-10,11-dihydro-5-oxo-5H-dibenzo[a,d]cycloheptene having a m.p. of 260.5°-262° C was obtained and from o-isopropylbenzaldehyde, 2-carboxy-9-isopropyl-10,11-dihydro-5-oxo-5-oxo-5H-dibenzo[a,d]cycloheptene having a m.p. of 230°-231° C was obtained.

EXAMPLE III — Wittig condensation

148 G. of 2-methylterephthalic acid was refluxed for 24 hrs. in 750 ml of dry methanol containing 30 ml of sulfuric acid. The solution was cooled, poured into water and extracted with ether. The extract was washed, dried and evaporated to give dimethyl-2-methylterephthalate.

88 G. of dimethyl-2-methylterephthalate in 1000 ml. of carbon tetrachloride containing 89 g. (1 eq.) of N-bromosuccinimide was refluxed for 3 hrs. using a heat lamp. The solution was cooled, filtered and evaporated to dryness to give dimethyl-2-bromomethylterephthalate.

25.7 G. of dimethyl-2-bromomethylterephthalate was refluxed in 250 ml of acetonitrile containing 26.2 g. (1 eq.) of triphenylphosphine for 4 hrs. The solution was cooled and diluted with 1250 ml of ether thereby precipitating 2,5-bis(carbomethoxy)-benzyltriphenylphosphonium bromide which was filtered off and dried under vacuum.

20 G. of 2,5-bis(carbomethoxy)benzyltriphenylphosphonium bromide and 7.65 g. of m-methoxybenzaldehyde were added to 100 ml of acetonitrile and 22 ml of diazabicyclononene was added. After 16 hours the mixture was added to water and extracted with ethyl acetate. The extract was washed, dried and evaporated. The residue was refluxed for 1 hour in 250 ml of methanol and 250 ml of water containing 10 g. of potassium hydroxide. The solution was cooled and extracted with chloroform. The aqueous layer was acidified with dilute hydrochloric acid and extracted with ethyl acetate. The extract was washed, dried and evaporated to afford cis and trans 3'-methoxystilbene-2,5-dicarboxylic acid. 7.8 G. of this compound was hydrogenated for 1½ hours in 800 ml of ethanol containing 1.5 g. of 5% palladium on carbon catalyst. The solution was filtered and evaporated to give 2-(m-methoxyphenethyl)-benzene-1,4-dicarboxylic acid which was cyclized according to the procedure set forth in Example I, A to afford 2-carboxy-8-methoxy-10,11-dihydro-5-oxo-5H-dibenzo[a,d]-cycloheptene having a m.p. of 220°-222° C. Similarly, other 8-substituted compounds of this invention may be obtained by reacting 2,5-bis(carbomethoxy) benzyltriphenylphosphonium bromide with a m-substituted benzaldehyde having a halogen such as fluoro, chloro or bromo, a lower alkyl of 1–4 carbons, or a lower alkoxy such as ethoxy, n-propoxy, isopropoxy, n-butoxy, isobutoxy, n-pentyloxy, n-hexyloxy and the like. By reacting an o-substituted benzaldehyde or a p-substituted benzaldehyde with 2,5-bis(carbomethoxy) benzyltriphenylphosphonium bromide a 2-carboxy-9-substituted-10,11-dihydro-5-oxo-5H-dibenzo[a,d]cycloheptene or a 2-carboxy-7-substituted 10,11-dihydro-5-oxo-5H-dibenzo[a,d]cycloheptene is obtained, respectively. For example 2-carboxy-7-methyl-10,11-dihydro-5-oxo-5H-dibenzo[a,d]cycloheptene having a m.p of 235° C was obtained from p-methylbenzaldehyde; 2-carboxy-8-methyl-10,11-dihydro-5-oxo-5H-dibenzo[a,d]cycloheptene having a m.p. of 196°-197° C was obtained from m-methylbenzaldehyde; and 2-carboxy-9-methyl-10,11-dihydro-5-oxo-5H-dibenzo[a,d]cycloheptene having a m.p. of 232°-234° C was obtained from o-methylbenzaldehyde.

EXAMPLE IV — Preparation of 2-carboxy-7-,8- or 9-hydroxy-10,11-dihydro-5-oxo-5H-dibenzo[a,d]cycloheptenes To 2.2 ml of concentrated hydrochloric acid and 2.0 ml of pyridine which were heated to 220° for 20 minutes, 2.00 g of 2- carboxy-7-methoxy-10,11-dihydro-5-oxo-5H-dibenzo[a,d]cycloheptene was added. The mixture was heated to 210°-215° for 90 minutes, then cooled and diluted with water. The product was filtered off and recrystallized from aqueous ethanol to give 2-carboxy-7-hydroxy-10,11-dihydro-5-oxo-5H-dibenzo[a,d]cycloheptene, m.p. 256°-257°. Similarly, the 8-hydroxy and 9-hydroxy compounds of this invention are obtained from 2-carboxy-8-methoxy-10,11-dihydro-5-oxo-5H-dibenzo[a,d]cycloheptene and 2-carboxy-9-methoxy-10,11-dihydro-5-oxo-5H-dibenzo[a,d]cycloheptene, respectively.

EXAMPLE V — Preparation of 2-carboxy-7-,8- or 9-alkoxy-10,11-dihydro-5-oxo-5H-dibenzo[a,d]cycloheptene 0.82 G. of 2-carboxy-7-hydroxy-10,11-dihydro-5-oxo-5H-dibenzo[a,d]cycloheptene was dissolved in 30 ml of ethanol and a solution of 1.0 g of potassium hydroxide in 5 ml of water was added, followed by 2.0 ml of isopropyl bromide. The reaction was refluxed for 3 hours, then diluted with water and acidified with dilute hydrochloric acid. The product was filtered off and recrystallized from aqueous dimethylformamide to give 2-carboxy-7-isopropoxy-10,11-dihydro-5-oxo-5H-dibenzo[a,d]cycloheptene, m.p. 174°-177°. By substituting other alkylbromides or iodides such as ethyl bromide, m-propyl bromide, isobutyl bromide, n-amyl bromide, n-hexyl bromide and the like, the corresponding 2-carboxy-7-alkoxy-10,11-dihydro-5-oxo-5H-dibenzo[a,d]cycloheptenes are obtained. The 8- and 9- alkoxy compounds are similarly prepared.

EXAMPLE VI — Interconversion of 7-,8- or 9-halo compounds 0.81 G. of 2-carboxy-9-bromo-10,11-dihydro-5-oxo-5H-dibenzo[a,d]cycloheptene and 0.32 g. of cuprous chloride were refluxed for 8 hours in 10 ml of N-methylpyrrolidinone. The solution was cooled and added to a solution of 4.4 g. of ferric chloride hexahydrate in 6 ml of water and 3 ml of concentrated hydrochloric acid. The mixture was heated to 90° for 1 hour, then was poured into water and filtered. The residue was recrystallized from aqueous dimethylformamide to afford 2-carboxy-9-chloro-10,11-dihydro-5-oxo-5H-dibenzo[a,d]cycloheptene, m.p. 258.5°-260°.

Similarly the 2-carboxy-7- or 8- chloro or iodo-10,11-dihydro-5-oxo-5H-dibenzo[a,d]cycloheptene may be obtained from the corresponding 7- or 8- bromo compound. For example, by following the above procedure, 2-carboxy-7-chloro-10,11-dihydro-5-oxo-5H-dibenzo[a,d]cycloheptene having a m.p. of 255°-256° C was obtained from the corresponding 7-bromo compound.

EXAMPLE VII — Preparation of 2-carboxy-7-,8- or 9-substituted-5-oxo-5H-dibenzo[a,d]cycloheptenes A solution of 1.49 g. of 2-carbomethoxy-9-fluoro-10,11-dihydro-5-oxo-5H-dibenzo[a,d]cycloheptene and 0.94 g. of N-bromosuccinimide in 100 ml of carbon tetrachloride was refluxed and irradiated with a 100 W incandescent lamp for 22 hours. The cooled solution was filtered and evaporated, and the residue dissolved in 25 ml of dimethylformamide. 1.5 Ml of diazabicyclononene was added and the mixture heated to 80° for 1 hours, then poured into dilute hydrochloric acid. The mixture was extracted with ethyl acetate and the extract washed, dried and evaporated. The residue was refluxed for 2 hours in 50 ml of water and 25 ml of methanol containing 1.5 g. of sodium hydroxide. The solution was cooled, acidified and filtered. The residue was recrystallized from aqueous dimethylformamide to yield 2-carboxy-9-fluoro-5-oxo-5H-dibenzo[a,d]cycloheptene, mp 340° (decomp.)

By following the above procedure the following compounds are representative of those which are prepared:
2-carboxy-9-chloro-5-oxo-5H-dibenzo[a,d]cycloheptene, m.p. 353°-355° C;
2-carboxy-9-bromo-5-oxo-5H-dibenzo[a,d]cycloheptene, m.p. 358° C (decomp.);
2-carboxy-8-fluoro-5-oxo-5H-dibenzo[a,d]cycloheptene, m.p. 251°-255° C;
2-carboxy-7-chloro-5-oxo-5H-dibenzo[a,d]cycloheptene;
2-carboxy-7-bromo-5-oxo-5H-dibenzo[a,d]cycloheptene;
2-carboxy-7-methoxy-5-oxo-5H-dibenzo[a,d]cycloheptene;
2-carboxy-7-isoproxy-5-oxo-5H-dibenzo[a,d]cycloheptene;
2-carboxy-7-methyl-5-oxo-5H-dibenzo[a,d]cycloheptene;
2-carboxy-7-isopropyl-5-oxo-5H-dibenzo[a,d]cycloheptene;
2-carboxy-9-methyl-5-oxo-5H-dibenzo[a,d]cycloheptene;

2-carboxy-9-isopropyl-5-oxo-5H-dibenzo[a,d]cycloheptene;

EXAMPLE VIII — Preparation of Alkyl esters of 7-, 8-, or 9-substituted 2-carboxy-5-oxo-5H-dibenzo[a,d]cycloheptenes and the corresponding 10,11-dihydro compounds A. 2.5 G. of 2-carboxy-9-chloro-5-oxo-5H-dibenzo[a,d]cycloheptene is dissolved in 50 ml of chloroform, and 5 ml of thionyl chloride and 0.1 ml of dimethylformamide are added thereto. The mixture is left for 8 hrs., then evaporated to dryness. The residue is dissolved in 50 ml of pyridine containing 10 ml of n-propanol. The mixture is heated to 75° C for 1 hr., then poured into water. The solution is extracted with ether and extract washed with dilute hydrochloric acid, dried and evaporated to yield the propyl ester of 2-carboxy-9-chloro-5-oxo-5H-dibenzo[a,d]cycloheptene.

In similar manner substituting methanol, 2-propanol, ethanol, butanol, 2-butanol, 3-methylbutanol, pentanol, 2-pentanol, 3-pentanol, 3-ethylpentanol, hexanol, 2-hexanol, 3-hexanol, heptanol, octanol, 2-octanol, 4-octanol, nonanol, 4-nonanol, 5-nonanol, decanol, 2-decanol, 3-decanol, 4-decanol, 5-decanol, undecanol, and dodecanol, the corresponding alkyl esters of 2-carboxy-9-chloro-5-oxo-5H-dibenzo[a,d]cycloheptene are obtained.

B. In similar manner, by substituting 2-carboxy-10,11-dihydro-5-oxo-5H-dibenzo[a,d]cycloheptenes substituted at the 7, 8 or 9 positions by chloro, fluoro, bromo, iodo, hydroxy, lower alkoxy, alkyl of 1 to 4 carbons, for the 2-carboxy-9-chloro-5-oxo-5H-dibenzo[a,d]cycloheptene of part A of this Example, the corresponding alkyl esters thereof are prepared.

EXAMPLE IX — Preparation of alkali metal salts

A. 30.0 G. of 2-carboxy-9-chloro-5-oxo-5H-dibenzo[a,d]cycloheptene is added to a mixture of 4.0 g. of sodium hydroxide in 500 ml of aqueous methanol. The mixture is stirred for 3 hrs. at room temperature, then the mixture is evaporated to afford the sodium salt of 2-carboxy-9-chloro-5-oxo-5H-dibenzo[a,d]cycloheptene. By employing 5.6 g. of potassium hydroxide in place of the sodium hydroxide above, there is obtained the potassium salt of 2-carboxy-9-chloro-5-oxo-5H-dibenzo[a,d]cycloheptene.

B. By employing the procedure of part A, sodium and potassium salts of other 2-carboxy-5-oxo-5H-dibenzo[a,d]cycloheptenes as well as 2-carboxy-10,11-dihydro-5-oxo-5H-dibenzo[a,d]cycloheptenes which are substituted at the 7, 8 or 9 position by fluoro, chloro, bromo, iodo, hydroxy, alkoxy of 1-6 carbons, or alkyl of 1-4 carbons substituents are prepared.

EXAMPLE X — Preparation of Calcium and Magnesium Salts

A. 24.0 G. of the sodium salt of 2-carboxy-9-chloro-5-oxo-5H-dibenzo[a,d]cycloheptene from Example IX in 1000 ml. of water is added to a mixture of 5.55 g. of calcium chloride in 300 ml of water, and the mixture is allowed to stand for 12 hrs. at room temperature. The mixture is then filtered, and the filtered salt washed several times with portions of ice cold water. The washed salt is dried under vacuum to yield the calcium salt of 2-carboxy-9-chloro-5-oxo-5H-dibenzo[a,d]cycloheptene.

Similarly, by using magnesium chloride the magnesium salt of 2-carboxy-9-chloro-5-oxo-5H-dibenzo[a,d]cycloheptene may be obtained.

B. By employing the procedure of part A of this Example, calcium and magnesium salts of 2-carboxy-5-oxo-5H-dibenzo[a,d]cycloheptenes and the corresponding 10,11-dihydro compounds which are substituted at the 7, 8 or 9 position by fluoro, chloro, bromo, iodo, hydroxy, alkoxy of 1-6 carbons, and alkyl of 1-4 carbons substituents are prepared.

EXAMPLE XI — Preparation of N-containing Organic Salts

A. 30.0 G. of 2-carboxy-9-chloro-5-oxo-5H-dibenzo[a,d]cycloheptene is added to mixture of 23.6 g. of procaine and 500 ml of aqueous methanol, and the mixture is stirred for 16 hrs. at room temperature. The mixture is evaporated under reduced pressure to afford the procaine salt of 2-carboxy-9-chloro-5-oxo-5H-dibenzo[a,d]cycloheptene.

B. In similar manner, substituting 14.6 g. of lysine, 17.4 g. arginine, 19.4 g. of caffeine, 6.1 g. of ethanolamine, 7.3 g. diethylamine, 12.2 g. tromethamine, 12.1 g. of choline 11.8 g. of 2-(diethylamino)ethanol, 8.9 g. of 2-(dimethylamino) ethanol, 19.5 g. methyl glucamine, or 6.0 g. of ethylenediamine, in place of the procaine above, the corresponding salts of 2-carboxy-9-chloro-5-oxo-5H-dibenzo[a,d]cycloheptene are obtained. Similarly other 2-carboxy-5-oxo-5H-dibenzo[a,d]cycloheptenes and the corresponding 10,11-dihydro compounds which are substituted at the 7, 8 or 9 position by fluoro, chloro, bromo, iodo, hydroxy, alkoxy of 1-6 carbons or alkyl of 1-4 carbons groups may be prepared.

EXAMPLE XII — Preparation of Dialkylamino Esters 1.0 G. of 2-chlorocarbonyl-9-chloro-5-oxo-5H-dibenzo[a,d]cycloheptene, as prepared in Example VIII, is dissolved in 10 ml. of anhydrous tetrahydrofuran with stirring, and treated with 2 ml. of dimethylethanolamine. After the solution is stirred for 16 hours, it is evaporated. The residue is partitioned between ether and dilute hydrochloric acid. The aqueous layer is basified with aqueous ammonia and extracted with ethyl acetate. This solution is evaporated and the residue chromatographed on silica gel, eluting with 10:90:1 methanol:chloroform-triethylamine, to afford the β-N,N-dimethylaminoethyl ester of 2-carboxy-9-chloro-5-oxo-5H-dibenzo[a,d]cycloheptene as an oil.

In similar manner substituting diethylethanolamine for the dimethylethanolamine, there is obtained the β-N,N-diethylaminoethyl ester of 2-carboxy-9-chloro-5-oxo-5H-dibenzo[a,d]cycloheptene.

Also in similar manner substituting 4-N,N-dimethylaminobutan-1-ol; 1-β-hydroxyethyl-2-imidazoline; 1-β-hydroxyethyl-3-methyl-2-imidazoline; 1-β-hydroxyethyl-pyrrolidine; 1-β-hydroxyethyl-2-methylpyrrolidine; 4-β-hydroxyethylmorpholine; 4-β-hydroxyethyl-3-methylmorpholine; 1-β-hydroxyethyl-4-methylpiperazine; and 1-β-hydroxyethyl-piperidine for the dimethylethanolamine there is obtained the corresponding 4'-N,N-dimethylaminobutyl ester; β-(2-imidazolin-1-yl)ethyl ester; β-(3-methyl-2-imidazolin-1-yl)ethyl ester; β-(pyrrolidin-1-yl)ethyl ester; β-(2-methylpyrrolidin-1-yl)ethyl ester; β-(morpholino)ethyl ester; β-(3-methylmorpholino)ethyl; β-(4-methylpiperazin-1-yl)ethyl ester; β-(piperid-1-yl)ethyl ester, respectively.

By substituting other 2-carboxy-5-oxo-5H-dibenzo[a,d]cycloheptenes and 2-carboxy-10,11-dihydro-5-oxo- 5H-dibenzo[a,d]cycloheptenes which are substituted at the 7-, 8- or 9-position with a halogen, lower alkyl of 1-4 carbons, lower alkoxy of 1-6 carbons, or hydroxy, other corresponding esters may be obtained.

EXAMPLE VIII — Histamine Aerosol Bronchoconstriction In The Guinea Pig

The following test is run to determine whether compounds show antihistamine or bronchodilation activity. The test is an indication of usefulness in treating asthmatic conditions. The compounds of this invention show antihistamine or bronchodilator activity.

Anoxic convulsions and unconsciousness which occurs in guinea pigs exposed to aerosolized histamine can be prevented by a drug having antihistamine or bronchodilator activity.

The guinea pigs are given orally a measured dose of a compound of this invention. The animals are then placed in a 1 gallon jar and exposed to a spray of 0.03% histamine diphosphate (calculated as base) delivered from a De Vilbiss No. 40 nebulizer until they showed a loss of righting or else they were removed after a 5 minute exposure. The percentage of animals which did not show a loss of righting ability after 5 minutes exposure to the histamine aerosol is an indication of the degree of protection against histamine-induced bronchoconstriction afforded by the test compound.

EXAMPLE XIV — Complement Inhibition

A. In vitro assay

Human complement (Cordis Laboratories) (25μl) plus an appropriate amount of the test compound, in buffered saline, are incubated in a centrifuge tube at 37° for 30 minutes, and then 50μl of a 2.5% suspension of $Cr^{51}$-tagged sheep red blood cells (SRBC) plus 50μl of rabbit anti-SRBC serum (diluted 1:20) are added. The mixture is then incubated at 37° for 30 minutes, and 1 ml of tris-buffered saline containing 0.1% gelatin, is added. The tube is then centrifuged at 2000 rpm for 10 minutes to separate the supernatant liquid from the cells. The supernatant and cells are each counted on a gamma counter. The percent hemolysis is calculated as $$100 \times \left( \frac{\text{Counts per minute (CPM) for supernatant}}{\text{CPM for supernatant + CPM for cells}} \right)$$

For active compounds, the percent hemolysis is reduced when compared to that of an identical preparation absent the test compound.

B. In vivo assay

Normal rats are passively sensitized on the side by intradermal injection of 0.1 ml of rabbit precipitating antibody. After 3 hours the rats are challenged by intravenous injection of 1.0 ml of 0.5% Evans blue, plus 1 mg. egg albumin, plus the test compound. After a further 30 minutes the diameter of the blue spot on the side of the animal is measured. The diameter of the spot is compared to that on the side of a control animal treated identically except that no test compound was administered. For active compounds, the diameter of the spot is reduced compared to the control animals.

Activity of the test compound in (A) and/or (B) indicates their utility in the therapy of auto-immune diseases. Compounds of this invention show significant activity in the in vitro and/or in vivo assay.

We claim as our invention;

1. A compound selected from the group of compounds represented by the formula

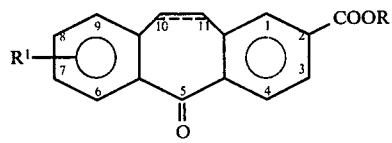

R is hydrogen or alkyl having one to twelve carbon atoms;
$R^1$ is at the 7, 8 or 9 position and is halogen, hydroxy, lower alkoxy of 1 to 6 carbon atoms inclusive or lower alkyl of 1 to 4 carbon atoms, inclusive;
the dotted lines represent an additional bond between the carbon atoms at the 10- and 11- positions; and the pharmaceutical acceptable salts thereof.

2. The compound of claim 1 wherein $R^1$ is fluoro at the 9 position and the bond between the carbons at 10- and 11- is a double bond.

3. The compound of claim 1 wherein $R^1$ is a chloro at the 9 position and the bond between the carbons at 10- and 11- is a double bond.

4. The compound of claim 1 wherein $R^1$ is bromo at the 9 position and the bond between the carbons at 10- and 11- is a double bond.

5. A compound selected from the group of compounds represented by the formula

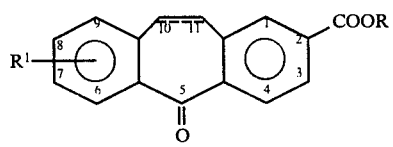

R is hydrogen or alkyl having 1 to 12 carbon atoms;
$R_1$ is fluoro, chloro or bromo at the 9 position; alkyl of 1, 2 or 3 carbon atoms at the 7- or 9-position; or isopropoxy at the 7 position; and
the pharmaceuticalaly acceptable salts thereof.

6. The compound of claim 5 wherein $R_1$ is fluoro at the 9 position.

7. The compound of claim 5 wherein $R_1$ is chloro at the 9 position.

8. The compound of claim 5 wherein $R_1$ is bromo at the 9 position.

9. The compound of claim 5 wherein $R_1$ is methyl at the 9 position.

10. The compound of claim 5 wherein $R_1$ is isopropyl at the 9 position.

11. The compound of claim 5 wherein $R_1$ is isopropyl at the 7 position.

12. A process for treatment of an asthmatic condition in an animal which comprises administering by inhalation to said animal an amount of the compound of claim 5 effective for relief of said asthmatic condition.

13. A pharmaceutical composition useful for treatment of an asthmatic condition which comprises a suitable pharmaceutical excipient and a compound of claim 5 present in an amount sufficient to give relief of said asthmatic condition.

* * * * *